United States Patent [19]
Vandewalle

[11] Patent Number: 5,993,452
[45] Date of Patent: Nov. 30, 1999

[54] CERCLAGE SYSTEM

[75] Inventor: Mark V. Vandewalle, Pierceton, Ind.

[73] Assignee: Biomet Inc., Warsaw, Ind.

[21] Appl. No.: 09/138,788

[22] Filed: Aug. 24, 1998

[51] Int. Cl.$^6$ .................................................. A61B 17/56
[52] U.S. Cl. ............................................. 606/74; 606/103
[58] Field of Search .................................. 606/74, 72, 60, 606/103, 76, 77

[56] References Cited

U.S. PATENT DOCUMENTS

| | | | |
|---|---|---|---|
| 2,987,062 | 6/1961 | Ellison | 606/74 |
| 3,654,668 | 4/1972 | Appleton . | |
| 4,146,022 | 3/1979 | Johnson et al. . | |
| 4,587,963 | 5/1986 | Leibinger et al. . | |
| 4,606,335 | 8/1986 | Weden . | |
| 4,612,923 | 9/1986 | Kronenthal | 606/77 |
| 4,667,662 | 5/1987 | Titone et al. . | |
| 4,976,712 | 12/1990 | VanderSlik . | |
| 4,988,350 | 1/1991 | Herzberg . | |
| 5,190,545 | 3/1993 | Corsi et al. . | |
| 5,324,307 | 6/1994 | Jarrett et al. . | |
| 5,417,690 | 5/1995 | Sennett et al. . | |
| 5,423,820 | 6/1995 | Miller et al. . | |
| 5,462,542 | 10/1995 | Alesi, Jr. . | |
| 5,536,270 | 7/1996 | Songer et al. . | |
| 5,665,088 | 9/1997 | Gil et al. | 606/69 |
| 5,665,089 | 9/1997 | Dall et al. . | |
| 5,693,046 | 12/1997 | Songer et al. . | |
| 5,702,399 | 12/1997 | Kipela . | |
| 5,741,260 | 4/1998 | Song et al. . | |
| 5,797,915 | 8/1998 | Pierson, III et al. | 606/74 |
| 5,810,824 | 9/1998 | Chan | 606/70 |

Primary Examiner—Michael Buiz
Assistant Examiner—Jonathan D. Goldberg
Attorney, Agent, or Firm—Ernest E. Helms; David L. Ahlersmeyer; Dean R. Golden

[57] ABSTRACT

A cerclage system for securing a fractured or weakened bone within a patient's body is provided. In a preferred embodiment the cerclage system includes a band formed to encircle the bone. Typically the band will be fabricated from a material having a high tensile strength such as a metal wire. A jacket supports the band in a spaced relationship from the bone. The jacket is resorbed by the patient's body.

15 Claims, 5 Drawing Sheets

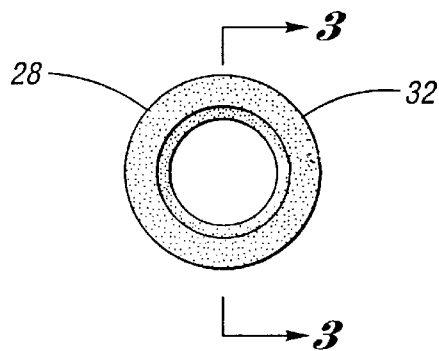
Fig. 2
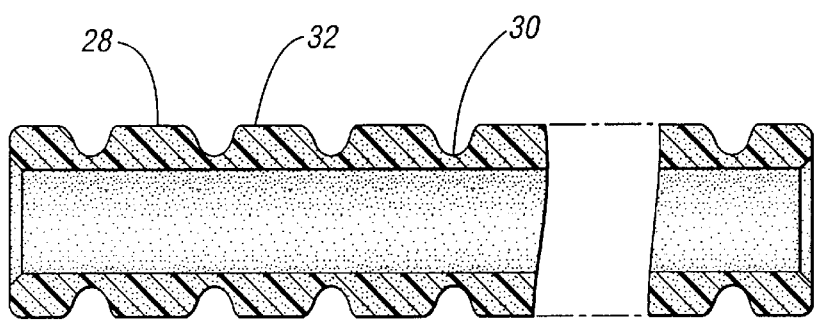
Fig. 3
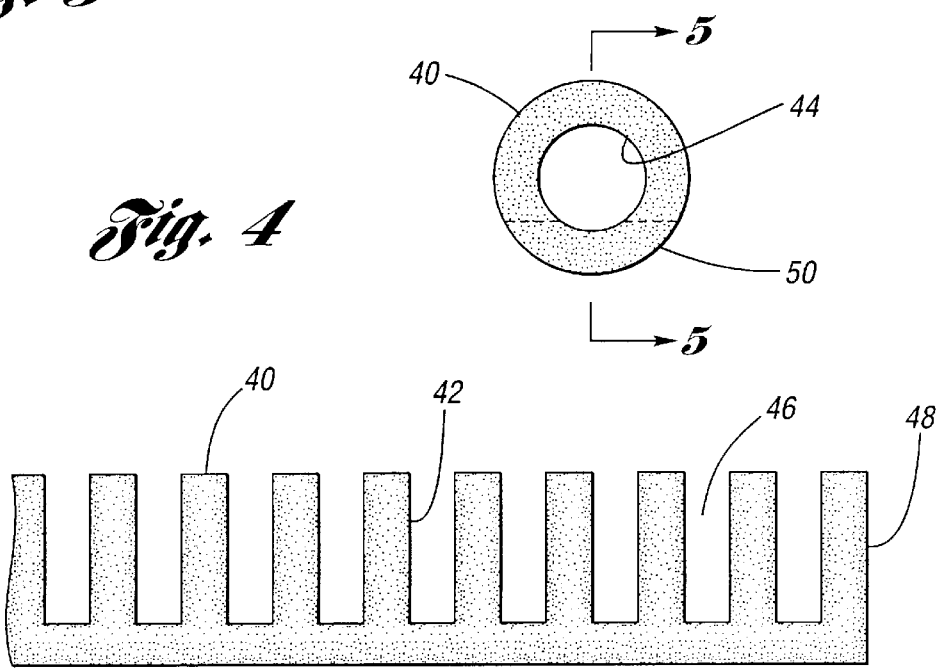
Fig. 4
Fig. 5

CERCLAGE SYSTEM

BACKGROUND OF THE INVENTION

The present invention relates to a cerclage system for the fixation of injured or fractured bones. The present invention also includes a method of treating injured or fractured bones utilizing a cerclage system. The present invention is particularly useful in the fixation of fractures of the femur and in prophylactic banding of the femur during press fit total hip replacement. The present invention can be used in the treatment of tibia fractures; stabilization of cortical onlay strut grafts; trochanteric reattachments; humerus, patella and ankle fractures. The present invention is also useful in the fixation of "soft" bones such as a sternum after open chest surgery.

In orthopedic surgery where severe breaks of bone have taken place, or in reconstructive procedures on bones, for example reconstructive hip procedures, a permanent cable implant is provided to hold bone portions together. During a total hip replacement, press fit femoral components are inserted into the canal of the femur, resulting in an extremely tight fit in many cases. Seating of the press fit components can sometimes result in the induction of large hoop stress in the proximal femur. To counterbalance the induced stress, a cerclage system is provided to apply a counteracting compressive hoop stress. The counteracting stress prevents crack formation and/or propagation.

To apply a sufficient compressive hoop stress, the band portion of the cerclage system is tightened around the bone and clamped in a tensionally stressed state. The band portion of the cerclage is typically provided by a metallic or fabric strip, or preferably a metallic wire or multi-filament cable.

However when the bone heals, the tight fit of the cerclage band around the bone may possibly induce indications of necrosis in the areas of the bone contacted by the cerclage band. Necrosis is caused when there is insufficient blood flow to the bone tissue. To counteract possible necrosis, some cerclage bands may have to be removed after the bone has healed, therefore requiring a later second operative procedure on the patient. Further complicating the second operative procedure is the fact that the bone tends to grow around the band and incorporate it. Therefore removal of the band can be difficult.

Prior attempts have been made to make a cerclage band of a resorable polymeric material. Unfortunately, most resorbable materials do not have sufficient tensile strength to allow them to be optimally utilized as a cerclage band. Therefore most cerclage bands are fabricated from metallic wires or cables. Still another limiting factor is the flexibility of the material which is a critical factor in the operative procedure. Most resorbable materials are not flexible enough for use as cerclage bands.

SUMMARY OF THE INVENTION

To overcome the above noted shortcomings of the prior art, the revelation of the present invention is brought forth. The present invention in a preferred embodiment provides a cerclage system for securing a fractured or weakened bone within a patient's body. The cerclage system includes a first member or band formed to encircle the bone. Typically the band will be fabricated from a material having a high tensile strength. A second member supports the band in a spaced relationship from the bone. The second member is resorbed by the patient's body to allow normal blood flow past the band after the bone has healed. If removal of the cerclage band is desired, removal is made easier by the fact that the bone will not be attached to the band or to the second member, since the second member is resorbed into the patient's body.

Various objects and advantages of this invention will become apparent to those skilled in the art from the following detailed description of the preferred embodiments, when read in light of the accompanying drawings.

BRIEF DESCRIPTION OF THE DRAWINGS

FIG. 2 is an enlarged end view of a tubular jacket in a free state which is utilized in the cerclage system shown in FIG. 1.

FIG. 3 is an enlarged sectional view of the aforementioned tubular jacket taken along lines 3—3. of FIG. 2.

FIG. 4 is an enlarged end view similar to that of FIG. 2 of an alternate preferred embodiment tubular jacket in a free state.

FIG. 5 is an enlarged sectional view of the tubular jacket shown in FIG. 4 taken along lines 5—5. of FIG. 4.

DETAILED DESCRIPTION OF THE PREFERRED EMBODIMENT

Figure 1:
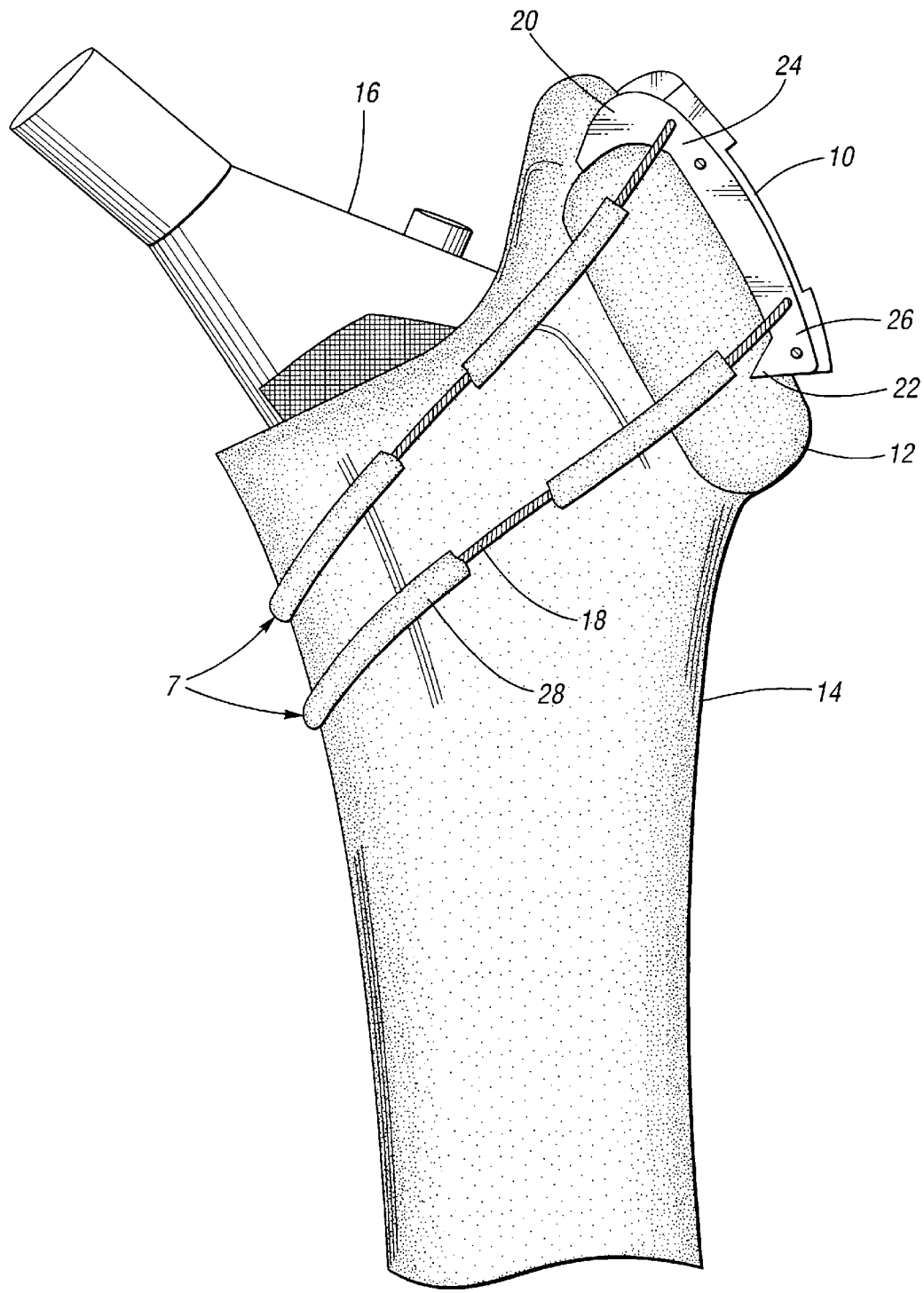
FIG. 1 is a perspective view of two preferred embodiment cerclage systems of the present invention used with a trochanteric grip to reattach a greater trochanter following osteotomy for total hip implant procedure.

Referring to FIG. 1, preferred embodiment cerclage systems 7 of the present invention are shown with a trochanteric grip 10 to reattach a greater trochanter 12 of a proximal femur 14. The cerclage systems 7 are applied following osteotomy for a total hip implant 16 procedure. The cerclage systems 7 are essentially identical. Each cerclage system 7 has a first member or band. As shown in FIG. 1, the band is provided by a wire 18. Typical wire materials are cobalt chrome or stainless steel. The material of wire 18 is selected to match the material of the trochanteric grip. A typical diameter for the wire 18 is 1.0 mm or less to insure flexibility of the wire. Proximal hooks 20 of the trochanteric grip reach over the top edge of the greater trochanter 12 and resist the pull of the abductor forces. Distal spikes 22 of the trochanteric grip 10 are embedded in the lateral surface of the greater trochanter 12 and provide rotational stability to the construct.

One end of each wire 18 is extended through a second member or jacket 28 before the opposite end of the wire 18 is looped through one of the proximal or distal locking crimps 24,26 (sometimes referred to as sleeves) of the trochanteric grip 10. Each jacket 28 supports a respective wire 18 in a spaced relationship from the proximal femur 14. Referring additionally to FIGS. 2 and 3, each jacket 28 in a free state has a tubular shape. The jacket is made from a resorbable polymeric material such as lactic acid or other suitable alternative. The jacket 28 has a tensile strength that is typically an order of magnitude less than the tensile strength of the wire 18. The jacket 23' can be one continuous piece as shown, or the jacket 28 can be cut up to provide a series of separate sections extended through by the wire 18. The jacket 28 has a series of annular grooves 30 on its outer diameter 32 to facilitate the bending required for the partial encircling of the proximal femur 14. Depending on the material and material thickness of the jacket 28, it may be preferable to independently heat the jacket 28 before the wire 18 is extended through the jacket 28. Heating the jacket 28 makes it more flexible. The jacket 28 has can interior dimension large enough for multiple passes of the wire 18 if a surgeon so desires. The jacket 28 as shown can accept three passes of the wire 18. In application the jacket 28 is advanced along the wire 18 as the wire 18 passes around the proximal femur 14. Each jacket 28 is selected of appropriate length (assuming a single piece application) or trimmed to the appropriate length such that the jacket 28 does not interfere with the respective locking crimp of the trochanteric grip 10. The wire 18 is then tightened using a standard tensioning tool. Since the wire 18 is not tensionally connected with the jacket 28, the wire 18 can be tensionally stressed an amount greater than the jacket 28 can tensionally withstand. The respective locking crimp is permanently deformed to permanently secure the wire 18 ends. Excess wire is trimmed from the respective locking crimp. The cerclage system 7 is now permanently closed and the proximal femur 14 is secured by the wire loop 18.

After time passes, the portion of the proximal femur 14 adjacent the implanted hip joint 16 and greater trochanter 12 heals. It is now beneficial for the permanently assembled cerclage wire 18 loop to loosen to avoid inadvertent long-term damage to the bone. The loosening is accomplished by the resorption of the jacket 28 by the patient's body. Resorption of the jacket 28 causes the wire 18 to no longer secure the proximal femur 14, thereby allowing normal blood flow past the respective wire 18. Necrosis of the proximal femur 14 is avoided. Also absorption of the jacket 28 prevents the bone from growing around the wire 18. Therefore if it is ever desirable in the future to remove the wire 18 because of an adverse reaction or another surgical procedure, the wire 18 may be easily removed.

Referring to FIGS. 4 and 5, an alternate preferred embodiment jacket 40 is provided. The jacket 40 can be formed from the same material as the jacket 28 previously described. The jacket 40 has a series of groves 42 which intersect with an interior 44 of the jacket 40 forming a series of parallel slots 46. The slots 46 form ribs 48 which are joined by a common aligned belt 50. The jacket 40 is very flexible when wrapped around the femur with the belt 50 of the jacket 40 positioned adjacent the proximal femur 14. In most instances preheating of the jacket 40 to achieve greater flexibility during application will not be required.

Figure 6:
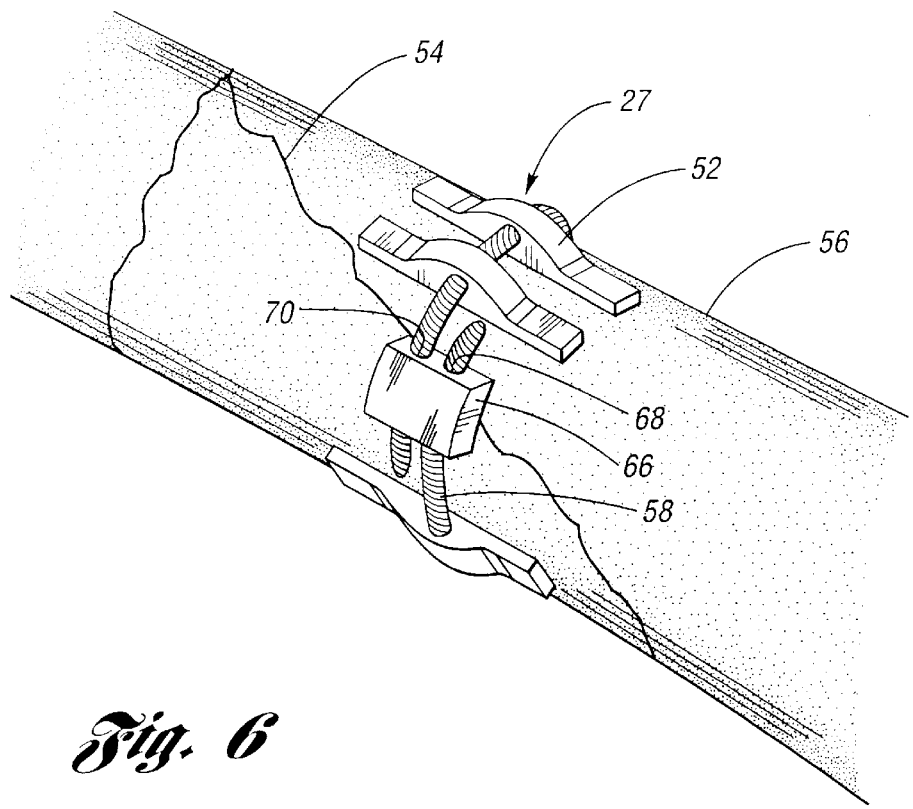
FIG. 6 is a perspective view of an alternate preferred embodiment cerclage system of the present invention which utilizes a plurality of resorbable directly contacting spacers for treating a fracture in a femur.
Figure 7:
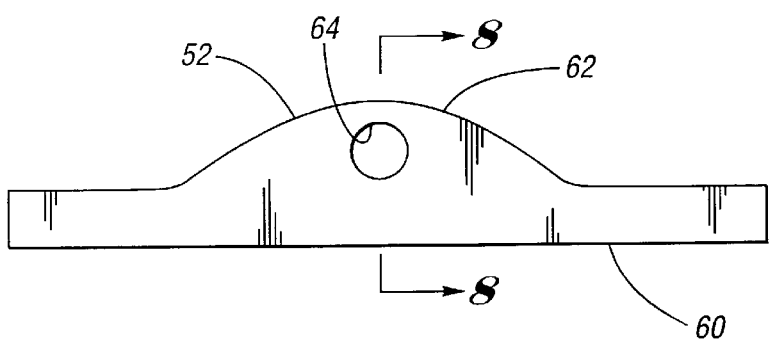
FIG. 7 is an enlarged front elevational view of the resorbable spacer shown in FIG. 6.
Figure 8:
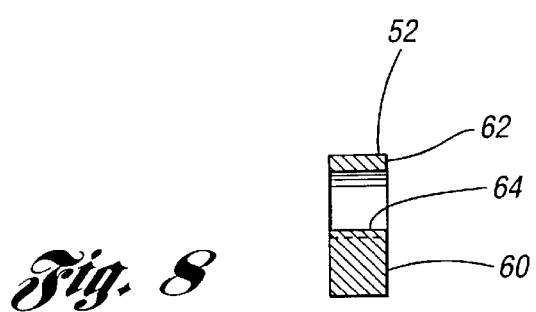
FIG. 8 is an enlarged side sectional view of the resorbable spacer shown in FIG. 6 taken along lines 8—8 of FIG. 7.

Referring to FIGS. 6–8, an alternate preferred embodiment cerclage system 27 of the present invention is shown which utilizes a plurality of resorbable directly contacting spacers 52 for treating a fracture 54 in a femur 56. In FIG. 6 only one of the cerclage systems 27 is shown. The band of the cerclage system 27 is provided by a multi-filament cable 58. A typical cable 58 will have a 7×7 construction. Seven wires are formed into a bundle. Seven bundles are combined into a cable 58. Typical cable materials are cobalt chrome or stainless steel. A preferred diameter for the cable 58 typically ranges from 1.6 mm to 2.0 mm. The cerclage system 27 also has a plurality of spacers 52. Each spacer 52 has a major dimension which is generally transverse to the cable 58. The spacers 52 have a base 60 oriented toward the femur 56. Opposite the base 60 is a head 62. The head 62 has an aperture 64 for the cable 58 to be inserted through. A surgeon can simply push the spacer 52 by hand on the cable 58 to position the spacer 52 in the desired location. The cerclage system 27 has an advantage in that the wide base 60 of the spacers 52 deliver the induced hoop stress to the femur 56 over a wider axial annular band of the femur 56 than a cerclage cable 58 without such spacers. In a typical operative procedure the spacers 52 are placed over one end of the cable 58 before the opposite ends of the cable 58 are placed into a locking crimp 66. The cable 58 is then tightened using the appropriate leans, and the locking crimp 66 is plastically deformed in an area adjacent the cable holes 68,70 to permanently close the cable 58 loop. Excess cable is then trimmed from the locking crimp 66. After time passes the deformity or linear fracture 54 (for which the cerclage system 27 is applied) heals. The cerclage cable 58 loop needs to loosen from the femur 56 to avoid inadvertent long-term damage to the femur 56. The loosening is achieved by the resorption of the spacers 52. In an embodiment of the cerclage system (not shown), the cerclage system has a cable supported by spacers similar to that shown in FIG. 6–8. Additionally the cerclage system has a bone plate (sometimes referred to as a cable plate) made according to Bailey U.S. Pat. No. 5,607,430, commonly assigned. The Bailey bone plate has a plurality of openings extending through an outer surface and a bone contact surface. The openings are located at positions along the length of material and are sized to receive a conventional bone screw. The outer surface of the bone plate is machined to include a plurality of integral locking clamp bosses positioned at locations along the length. Each of the locking clamp bosses has crimping surfaces and a pair of holes therethrough that are sized to receive the cable ends. Each of the locking clamp bosses is deformable to clamp the cable ends received in the pair of holes when the crimping surfaces are crimped. The integration of the locking crimps with the bone plate better facilitates handling of the bone plate and cerclage system during implantation procedures and substantially reduces the breakage a:d wear problems associated with prior art bone plates.

Figure 9:
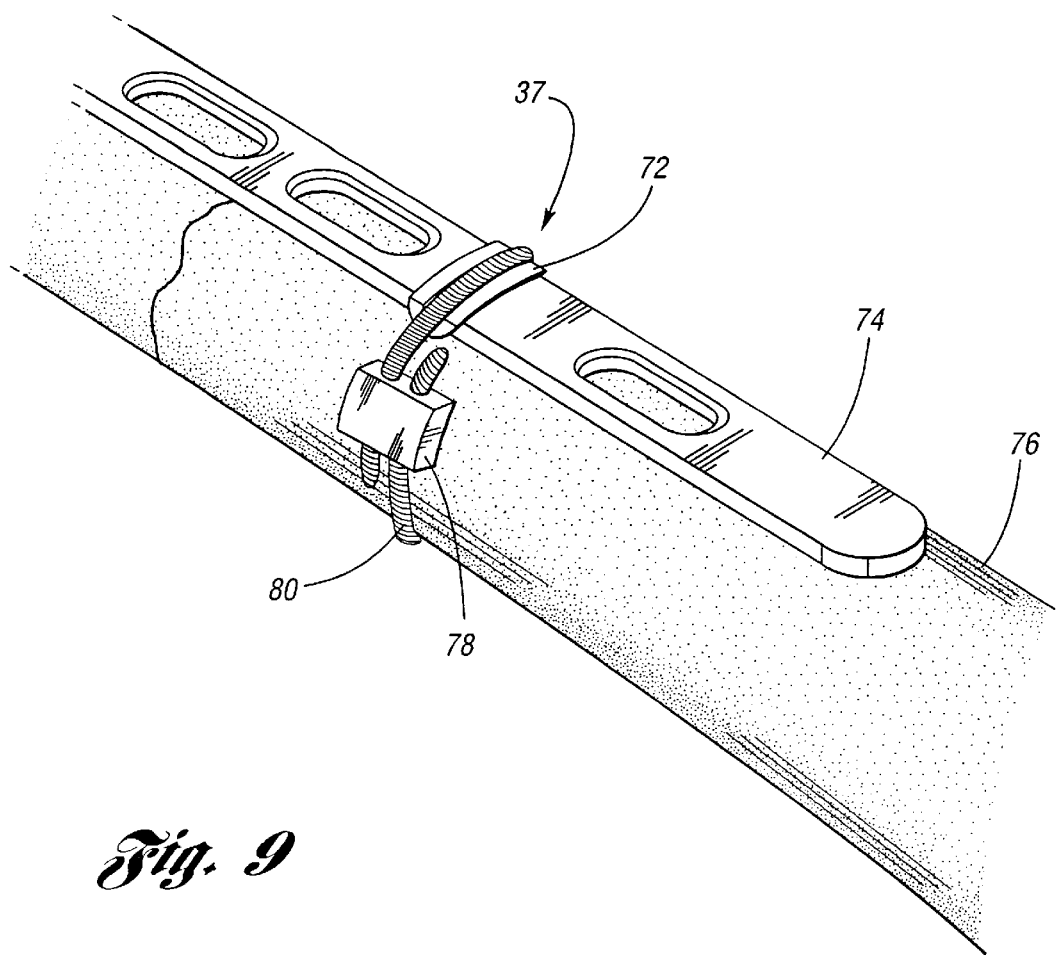
FIG. 9 is a perspective view of an alternate preferred embodiment cerclage system of the present invention which utilizers a resorbable spacer with a bone plate interposed between the resorbable spacer and a femur.

FIG. 9 is a perspective view of an alternate preferred embodiment cerclage system 37 of the present invention which utilizes a resorbable spacer 72 with a third member or bone plate 74 interposed between a resorbable spacer and a femur 76. Therefore the resorable spacer contacts the femur 76 via the bone plate 74. In the example of the present invention shown in FIG. 9, portions of the bone plate 74 which are not shown can be attached to the femur 76 by other cerclage systems (especially like the cerclage system previously described with spacers shown in FIGS. 6–8) or by bone screws. The proximal portion of the bone plate 74 is secured with the cerclage system 37 because the presence of an intramedulary stem precludes the use of bone screws. The cerclage system 37 locking crimp 78 is not integral to the bone plate 74. The spacer 72 is sized so as not to interfere with the securing of the locking crimp 78 to the cable 80.

Optionally the bone plate 74 can be transversely notched to axially fix the position of the spacer 72 (and cable 80) on the bone plate 74. In an embodiment not shown, the cerclage system shown in Fig, 9 can additionally have a jacket or spacers as shown in FIGS. I or 6 to further assure that the cable 80 loop is loose around the femur 76 when the femur 76 heals. If removal of the bone plate 74 is desired, the loosening of the cerclage system 37 makes bone plate 74 removal easier. Additionally, since no bone screw has been applied adjacent the cerclage system 37, any effort associated with bone screw removal to allow bone plate removal is eliminated.

Figure 10:
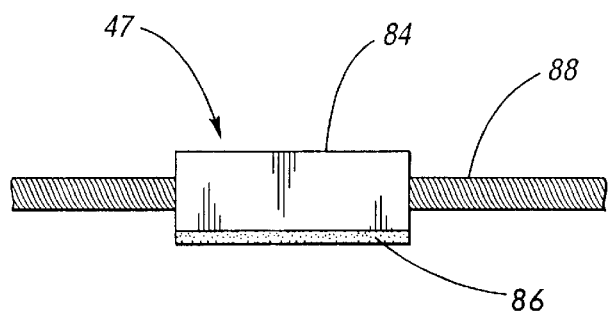
FIG. 10 is a side elevational view of an alternate preferred embodiment cerclage system of the present invention which utilizes a cable locking crimp with a connected resorbable spacer.

FIG. 10 is a side elevational view of an alternate preferred embodiment cerclage system 47 of the present invention which utilizes a clamping device or cable locking crimp 84 with a connected resorbable spacer 86. The cerclage system 47 has the advantage of minimizing possible interference of the spacer 86 with connection of the cable 88 to the locking crimp 84. In application, the locking crimp 84 may be positioned directly contacting a bone or on a bone plate. The spacer 86 may be clipped onto (by clips not shown) the locking crimp 84 or molded if desired. As will be apparent to those skilled in the art, the spacer 86 and locking crimp 84 of the cerclage system 47 can also be in combination with the previously described cerclage system jacket or spacers.

Figure 11:
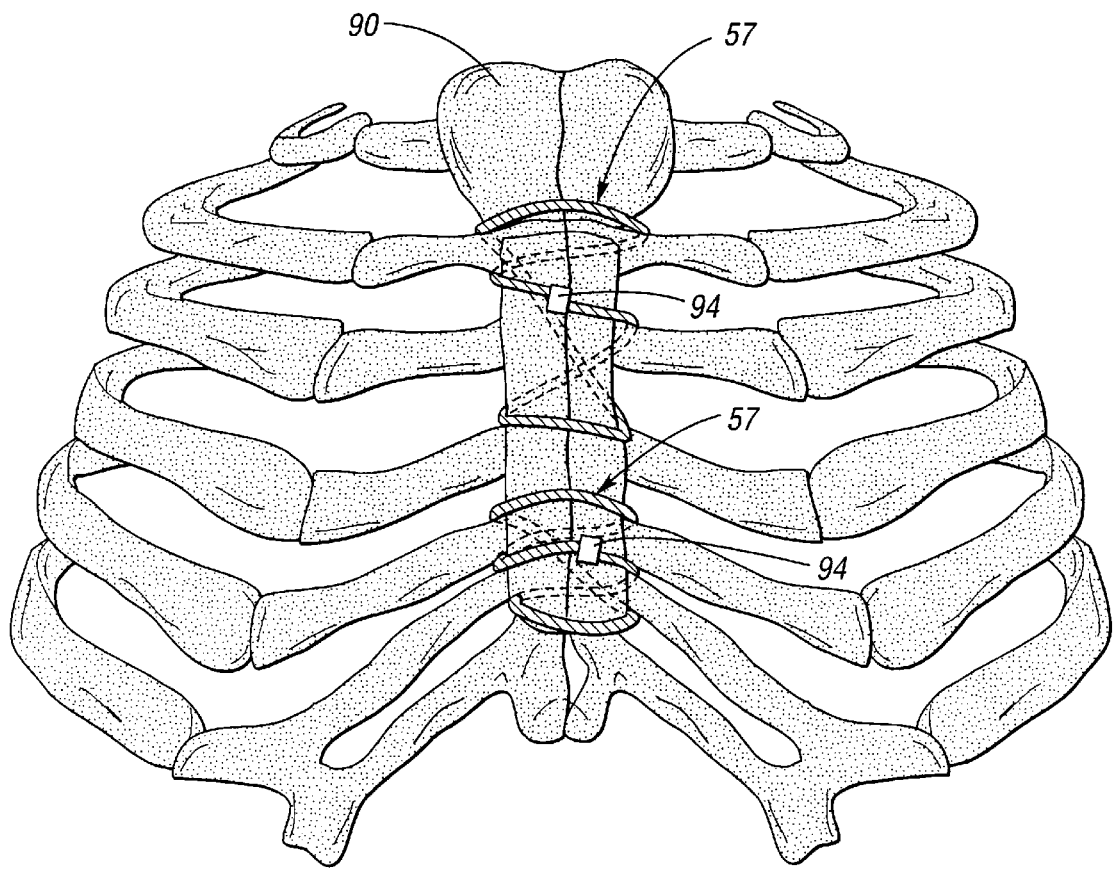
FIG. 11 is a perspective view of an alternate preferred embodiment cerclage system of the present invention which includes a multi-filament metallic cable having a resorbable coated sleeve, which is utilized to close a sternum of an open heart surgery.
Figure 12:
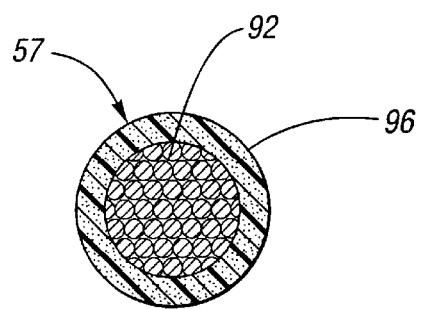
FIG. 12 is an enlarged sectional view of the cable shown in FIG. 10.

Referring to FIGS. 11 and 12, surgery in and adjacent to the heart generally requires the central opening of the sternum to provide the surgeon with access. The access is provided by longitudinally splitting the sternum bone 90. After surgery, the sternum bone 90 is rejoined and closed securely by two cerclage systems 57 of the present invention. Each cerclage system 57 has a multi-filament cable 92. Extreme ends of the cable 92 are joined by a locking crimp 94. The cable 92 has a resorbable coated jacket 96. An interface between the jacket 96 and the cable 92 is sterilized by a suitable technique. The resorbable jacket 96 is advantageous in that it will cause the looped cable 92 to loosen upon healing of the sternum bone 90. Also the jacket 96 also aids in the prevention of the cable 92 injuring any surrounding tissue during the application of the cerclage system 57. Still another advantage of the cerclage system 57 is that the jacket 96 material may be dyed a color that is more visually distinguishable than the cable 92, making application of the cerclage system 57 easier.

The principal and mode of operation of this invention have been explained and illustrated in its preferred embodiments which utilize multifilament cables. However it must be understood that this invention may be practiced otherwise with monofilament metal wire, metal bands such as Parham bands, polymer bands and fabric or braided polymer without departing from the spirit or scope of this invention.

What is claimed is:

1. An apparatus for securing a fractured or weakened bone within a patient's body, comprising:
   an elongated first member formed to circle the bone, the first member having first and second ends; and
   a second member operable for supporting said first member in a spaced relationship from the bone, said second member having a base oriented toward the bone and said second member having a head with an aperture through which the first member is inserted through, and said second member being independent of said first and second ends of said first members, wherein said second member is operable to be resorbed by a patient's body.

2. An apparatus as described in claim 1 wherein said first member is tensionally stronger than said second member.

3. An apparatus as described in claim 1 wherein said first member is formed from a metal.

4. An apparatus as described in claim 3 wherein said metal is a wire.

5. An apparatus as described in claim 1 wherein said second member has a major dimension generally transverse to said first member.

6. An apparatus as described in claim 1 wherein there are a plurality of said second members.

7. An apparatus for securing a fractured or weakened bone within a patient's body, comprising:
   a first member formed to encircle the bone, said first member having first and second ends; and
   a tubular second member encircling said first member, and said second member being slidable upon said first member with respect to said first member first and second ends operable for supporting said first member in a spaced relationship from the bone, wherein said second member is operable to be resorbed by a patient's body.

8. An apparatus as described in claim 7 wherein said second member has an inner dimension large enough for multiple passes of said first member.

9. An apparatus as described in claim 7 wherein said second member has grooves to facilitate bending of said second member around a patient's bone.

10. A cerclage system for securing a fractured or weakened bone within a patient's body, comprising:
    a first member formed by a wire to circle the bone;
    a second tubular member formed from a polymeric material, the second member having a series of annular grooves to facilitate the partial encircling of the bone by said second member, said first member extending through said second member, and said second member supporting said first member in a spaced relationship from the bone, wherein said second member is operable to be resorbed by the patient's body to allow normal blood flow past said first member after the bone has healed.

11. A cerclage system as described in claim 10 wherein said wire is a metallic wire.

12. A cerclage system as described in claim 10 wherein said second member has an interior dimension large enough for multiple passes of said first member.

13. An apparatus for securing, a fractured or weakened bone within a patient's body, comprising:
    a first member formed to circle the bone, said first member having first and second ends; and
    a tubular second member encircling said first member, and said second member being slidable upon said first member with respect to said first member first and second ends operable for supporting said first member in a spaced relationship from the bone, said second member is operable to be resorbed by a patient's body whereby said first member is no longer securing the bone after the bone has healed.

14. An apparatus for securing a fractured or weakened bone within a patient's body, comprising:
    a first member formed to circle the bone;
    a second member operable for supporting said first member in a spaced relationship from the bone, wherein said second member is operable to be resorbed by a patient's body; and
    a third member contacting the bone and contacting the second member generally opposite said first member.

15. An apparatus for securing a fractured or weakened bone within a patient's body, comprising:

an elongated first member formed to circle the bone having a first tensile strength; and a second member coated onto and encircling said first member operable for supporting said first member in a spaced relationship from the bone, wherein said second member is operable to be resorbed by a patient's body.

* * * * *